United States Patent [19]

Abraham et al.

[11] Patent Number: 5,102,670
[45] Date of Patent: Apr. 7, 1992

[54] METHOD FOR TREATING EYE DISORDERS BY REDUCING 12(R)-HYDROXYEICOSATETRAENOIC ACID AND 12(R)-DIHYDROXYEICOSATRIENOIC ACID LEVELS LEVELS

[76] Inventors: Nader G. Abraham, 243 Charter Cir., Ossining, N.Y. 10562; Michal L. Schwartzman, 415 Old Country Rd., Elmsford, N.Y. 10523; Michael W. Dunn, 1073 North Ave., New Rochelle, N.Y. 10804; Richard D. Levere, 5 Seymour Pl. W., Armonk, N.Y. 10504

[21] Appl. No.: 583,186

[22] Filed: Sep. 14, 1990

[51] Int. Cl.5 .................... A61K 33/24; A61K 33/32; A61K 31/70; A61K 31/555
[52] U.S. Cl. .................................. 424/650; 424/639; 424/641; 424/644; 424/646; 424/651; 424/654; 514/52; 514/185
[58] Field of Search ............... 424/650, 639, 641, 644, 424/646, 651, 654; 514/52, 185, 912

[56] References Cited

PUBLICATIONS

Abraham et al., Inv. Ophthal & Vi. Sci., 28(9): 1464–1472 (1987).
Abraham et al., Int. J. Biochem., 20(6): 543–558 (1988).
Sacerdoti et al., Science, 243: 388–390 (1-20-89).
Masferrer et al., Inv. Ophthal & Vis. Sci., 30(3): 454–460 (Mar. 1989).
Masferrer et al., Inv. Ophthal & Vis. Sci., 31(3): 535–539 (Mar. 1990).
Chemical Abstract, 109:27622m (1988), Zhuang.
Chemical Abstract, 100:186402u (1984), McCarty.

*Primary Examiner*—Frederick E. Waddell
*Assistant Examiner*—Zohreh A. Fay
*Attorney, Agent, or Firm*—Felfe & Lynch

[57] ABSTRACT

The invention relates to a method for treating or preventing ocular swelling and corneal-conjunctival inflammation. This is accomplished by administering to the eye of a subject, either before or after exposure to an ocular swelling stimulus, an amount of a heme oxygenase inducing agent sufficient to increase levels of heme oxygenase in the eye and thereby to reduce or to regulate the amount of 12(R) hydroxyeicosatetraenoic and 12(R) DiHETE acids present. Particularly preferred agents include stannous compounds, such as $SnCl_2$, other metals, heme derivatives and Vitamin B12. These compounds may be administered in various forms.

16 Claims, No Drawings

METHOD FOR TREATING EYE DISORDERS BY REDUCING 12(R)-HYDROXYEICOSATETRAENOIC ACID AND 12(R)-DIHYDROXYEICOSATRIENOIC ACID LEVELS LEVELS

FIELD OF THE INVENTION

This invention relates to methods for treatment of eye disorders. More particularly, it relates to methods for alleviating or eliminating conditions characterized by corneal swelling and corneoconjunctival inflammation (red eye). This is accomplished by administering a physiologically acceptable heme oxygenase inducer to the eye of a subject, in an amount sufficient to induce heme oxygenase production. In turn, the enzyme reduces the level of 12(R)-hydronyeicosatetraenoic and 12(R)Dihydroxy-eicosatrienoic acids in the cornea, which in turn reduce the inhibition of ATPase in the eye and vasodilation of conjunctival blood vessels, breakdown of the blood aqueous barrier, chemotaxis of inflammatory leukocytes, new blood vessel invasion of the cornea and morphologic changes in the corneal endothelium. The decrease in inhibition in turn leads to the decrease in swelling and edema. The decrease in 12(R)Di-hydroxyeicosatrienoic acid leads to diminished inflammation in the conjunctiva and cornea.

BACKGROUND AND PRIOR ART

Heme oxygenase is an enzyme which was first implicated in the degradation of molecules of heme into biliverdin. Abraham et al., Int. J. Biochem 20(6): 543–558 (1988), the disclosure of which is incorporated by reference herein. The enzyme was recognized to be inducible by heavy metals, such as Cr, Mn, Fe, Ni, Cu, Zn, Au, Hg, Pb, Cd, Sn, Pt, and Sb. However, cobalt is regarded as the most powerful inducer of the enzyme, and has been seen to induce a 45 fold increase in the enzyme. The enzyme is also induced by heme derivatives and by vitamin B12. Abraham, supra. The enzyme was recognized in human corneal epithelium, as per Abraham et al., Inv. Ophthal & Vis. Sci. 28(9): 1464–1472 (1987). This paper suggests that the enzyme is implicated in drug detoxification in the corneal epithelium, a phenomenon that had been observed prior to this paper. Abraham et al. also note that levels of the enzyme cytochrome P-450 monooxygenase are dependent upon heme oxygenase levels and that the P-450 monooxygenase enzyme is implicated in the metabolism of arachidonic acid. Two metabolites are noted in particular and, while not identified, one metabolite is characterized as an Na+-K+ATPase inhibitor, and the other as a vasodilator. Masferrer et al. in Inv. Opthal & Vis. Sci. 31(3): 535–539 (March, 1990), identify the Na+-K+ATPase inhibitor as 12(R)-hydroxy-eicosatetraenoic acid, and this will be described as "12(R)-HETE" hereafter. Masferrer et al. show that upon administration of 12(R)HETE to rabbits having normal intraocular pressure (IOP), the pressure dropped, dramatically. IOP, as will be recognized to the skilled artisan, is a condition characterized by a relationship between aqueous humor production and drainage. Thus, Masferrer et al. taught that some ocular disorders could be treated via the administration of 12(R)HETE.

Masferrer et al., in an earlier paper, i.e., Inv. Ophthal. & Vis. Sci 30(3); 454–459 (1989) identified the previously mentioned vasodilator as 12-hydroxy-5,8,14-eicosatrienoic acid (12(R)DIHETE). This paper suggested the administration of this compound, referred to as "12-DIHETE" hereafter, would provoke massive vasodilation of conjunctival blood vessels in the eye, breakdown of the blood aqueous barrier, chemotaxis of inflammatory leukocytes and invasion of the cornea by new blood vessels. Up to a 30-fold increase of aqueous humor protein was observed.

The previously described inducibility of heme oxygenase by heavy metals, certain metalloporphyrins and vitamin B12 is of relevance in connection with Sacerdoti et al., Science 234: 388–390 (1989). This paper noted an increase in the metabolites of arachidonic acid in the kidneys of spontaneously hypertensive rats. Treatment with stannous chloride, ($SnCl_2$) was found to deplete the renal cytochrome P-450, and to return the blood pressure of the subject animals to a normal level.

In view of the art on 12(R)-HETE and heme oxygenase, it was therefore surprising that eye disorders characterized by ocular swelling could be treated by administering a compound which, ultimately, reduces the level of 12(R)-HETE in the eye. This is surprising because the art would seem to suggest that 12(R)-HETE could be added to the eye to reduce IOP. It was not taught or suggested, however, that manipulation of the heme oxygenase pathway could eventually decrease the amounts of 12(R)-HETE and 12(R)-DIHETE, with an observable physiological effect. It is this effect which is the subject of the invention, and which will be explained in greater detail in the description which follows.

DETAILED DESCRIPTION OF PREFERRED EMBODIMENTS

This invention is premised on the discovery of the interrelationship of various components of an enzymatic pathway. Specifically:

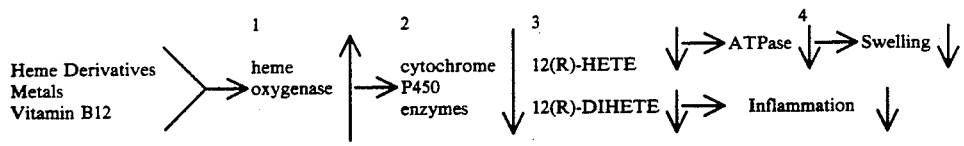

In the foregoing schematic, the relationship may be explained as follows. The presence of a heme oxygenase inducer, such as a metal ion, increases the activity and amount of heme oxygenase present. The compounds 12(R)-HETE and 12(R)DIHETE are present due to the arachidonic metabolism pathway described supra. Thus, when cytochrome-P450 monooxygenase is present, which is the case in the eye, the two related compounds 12(R)-HETE and 12(R)-DIHETE are produced. These compounds, as has been explained supra, have different effects on the eye, with 12(R)-HETE acting to inhibit ATPase and 12(R)DIHETE acting as vasodilator and inflammatory mediator. When ATPase is inhibited, swelling results.

The new and surprising step in this pathway, however, involves "2", i.e., the discovery that an increase in hemeoxygenase will lead to a decrease in 12(R)-HETE and 12(R)-DIHETE. Thus, by inducing heme oxygenase production, one shuts down or slows down steps "3" and "4" in the pathway.

To that end the invention is directed to a method for reducing or alleviating ocular swelling and ocular inflammation caused by 12(R)HETE and 12(R)DIHETE by administering to a patient with this type of swelling a heme oxygenase inducer, such as the metal ions described supra. These inducers are administered, e.g., in the form of metal ion containing compounds, and in an amount sufficient to induce heme oxygenase levels with concurrent decreases in levels of 12(R)-HETE. Compounds such as heme derivatives may be used, including synthetic hemes. Synthetic hemes include a wide variety of metalloporphyrins in which the chelated atom is a metal other than iron such as tin, chromium, cobalt, zinc or manganese or analogous compounds in which the porphyrin ring structure is modified as in protoporphyrins or mesoporphyrins. Typical synthetic hemes which might be mentioned by way of example are tin protoporphyrin (SnPP), tin mesoporphyrin (SnMP), tin diiododeuteroporphyrin ($SnI_2DP$) and the corresponding zinc, chromium, manganese and cobalt compounds all of which are known or can be prepared by known procedures. All are useful in the practice of this invention.

Other heme derivatives useful in the practice of the invention include acid addition salts of heme, particularly amino acid salts or heme including L-amino acids such as arginine. Heme arginate is especially preferred for use in the invention, although other non-toxic acid addition salts or inorganic and organic acids may also be employed.

Of course, any inducer must be one which is physiologically acceptable, as this phrase is used in the art, to the subject organism. In addition, the amount administered will vary, depending upon the degree of swelling, the patient or subject's general condition, and so forth.

Particularly preferred therapies comprise the administration of physiologically acceptable stannous compounds, i.e., compounds containing $Sn^{2+}$ ions, such as stannous chloride. Other sources of the previously listed metal ions will be known to the skilled artisan, and will not be repeated here.

The mode of administration will vary, but given the composition of the eye, such as the human eye, the preferred mode is a liquid form. Eye drops and eye washes are examples of such liquid forms of administration, as are saline solutions which are pharmacologically acceptable to the eye. Thus, the metal ion containing compounds may be administered in conjunction with a pharmacologically acceptable carrier.

In another mode of administration, the inducer may be administered in the form of a time release system, such as a contact lens, bandage lens or wafer. Such systems are well known to the ophthalmological art, and are used when a uniform, controlled delivery of the drug is desired. These systems may be made by materials which dissolve in the eye, and, again, are subject to the same pharmacologically acceptable requirements as are indicated for the aforementioned solutions.

The invention also relates to prevention of ocular swellings by administration of the compound prior to, or simultaneously with exposure of the subject to a condition where ocular swelling is expected. Situations in which corneal swelling is anticipated would call for prior or simultaneous administration of the compound. The latter case provides an especially attractive situation for the use of time release implants, as the wearer need not constantly administer the material.

"Ocular swelling" as used herein refers to any condition in which the eye or parts thereof, such as the cornea, are subject to swelling, such as a cornea edema.

The following example is provided to show one embodiment of the invention but shall in no way be seen to limit the scope of the preceding disclosure.

EXAMPLE

Corneal epithelial hypoxia induced by gas impermeable scleral contact lenses causes a 21 fold increase in 12(R)HETE production at 4 hours; a 5 fold increase of both metabolites 12(R)HETE and 12(R)-DIHETE at 6 hours and an 18 fold increase of 12(R)DIHETE at 144 hours. Davis et al., Invest Optical Vis. Sci. 31, page 406 (1990). Corneal epithelial edema indicated by biomicroscopic observation of the typical ground glass appearance of the swollen epithelium can be seen at 2 hours along with conjuctival vasodilation. Invasion of new vessels from the limbus is prominent at 144 hours.

Gas impermeable scleral contact lenses were placed in each eye of 6 rabbits. A 95% water content collagen lens hydrated in a solution containing 100 µg/ml of $SnCl_2$ was placed under the gas impermeable lens on the covered surface in half of these eyes simultaneously with the placement of the gas impermeable lens. At 2 hours in the treated group corneal epithelial edema was absent and the conjunctival vasodilation greatly reduced; at 144 hours no new vessels were seen in the cornea of the treated eyes in contradistinction to the control eyes which were highly vascularized.

This example shows that the $SnCl_2$ trated eyes showed reduction in swelling, as compared to those which did not receive it. There was no epithelial edema, nor was there neovascularization. In addition, the increased levels of the two metabolites also decreased.

The dosage used herein, 100 µg/ml of the active ingredient, will vary from subject to subject and condition to condition; however, a range of from about 10 µg to about 2000 µg/ml of the active compound is not unreasonable, assuming that the compound is physiologically acceptable to the subject, and the amount is effective to treat the subject individual.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. Method for reducing ocular swelling in a subject comprising administering to the eye of a subject in need of reduced ocular swelling an amount of a physiologically acceptable heme oxygenase inducer in an amount sufficient to induce increased production of heme oxygenase and to reduce the amount of 12(R)- hydroxyeicosatetraenoic acid present in said eye.

2. Method of claim 1, wherein said inducer is a metal ion containing compound, heme derivative or vitamin B12.

3. Method of claim 2, wherein said metal ion containing compound contains an ion of a metal selected from the group consisting of Cr, Mn, Fe, Ni, Cu, Zn, Au, Hg, Pb, Cd, Sn, Pt and Sb.

4. Method of claim 3, wherein said metal ion is $Sn^{2+}$.

5. Method of claim 2, wherein said metal ion containing compound is SnCl$_2$.

6. Method of claim 1, wherein said subject is a human being.

7. Method of claim 1, wherein said inducer is administered in the form of a liquid.

8. Method of claim 7, wherein said liquid is an eye wash, eye drops, or saline solution.

9. Method of claim 1, wherein said inducer is administered in the form of a time release system.

10. Method of claim 9, wherein said time release system is a dissolvable contact lens, bandage lens or wafer.

11. Method for preventing ocular swelling in a subject comprising administering to a subject an amount of a physiologically acceptable inducer of heme oxygenase in an amount sufficient to induce increased production of heme oxygenase and to regulate the amount of 12(R)-hydroxyeicosatetraenoic acid present in the eye upon exposure of said eye to a stimulus which provokes ocular swelling.

12. Method for reducing inflammation in the cornea or conjunctiva caused by 12(R)Dihydronyeicosatrienoic acid comprising administering to a subject in need of reduction of said corneal or conjunctival inflammation an amount of a physiologically acceptable heme oxygenase inducer sufficient to induce increased production of heme oxygenase and to reduce the amount of 12(R)dihydroxy-eicosatrienoic acid present in said eye.

13. Method of claim 12, wherein said inflammation is caused by conjunctival vasodilation.

14. Method of claim 12, wherein said inflammation is caused by blood/aqueous barrier breakdown.

15. Method of claim 12, wherein said inflammation is caused by chemotaxis of leukocytes.

16. Method for treating a condition selected from the group consisting of hyphema, subconjunctival hemorrhage, and corneal blood staining comprising administering to a subject with said condition an amount of pharmacologically acceptable heme oxygenase inducer sufficient to induce increased production of heme oxygenase and to convert heme to biliverdin.

* * * * *